United States Patent [19]
Beehler et al.

[11] Patent Number: 5,607,446
[45] Date of Patent: Mar. 4, 1997

[54] PUPIL DILATOR

[76] Inventors: Cecil C. Beehler, 5546 Shaddelee Dr., Fort Myers, Fla. 33907; Cecil C. Beehler, II, 4610 NW. 35th Rd., Gainesville, Fla. 32606

[21] Appl. No.: 381,333

[22] Filed: Jan. 31, 1995

[51] Int. Cl.$^6$ ............................................. A61B 17/00
[52] U.S. Cl. ....................... 606/198; 600/206; 604/107
[58] Field of Search ............................ 606/194–198, 606/206; 604/104–108; 600/204–206, 236

[56] References Cited

U.S. PATENT DOCUMENTS

| | | | |
|---|---|---|---|
| 4,654,028 | 3/1987 | Suma | 604/187 |
| 4,909,789 | 3/1990 | Taguchi et al. | 606/198 |
| 5,195,506 | 3/1993 | Hulfish | 600/206 |
| 5,450,842 | 9/1995 | Tovey et al. | 600/204 |

*Primary Examiner*—Michael Buiz
*Assistant Examiner*—William W. Lewis
*Attorney, Agent, or Firm*—William E. Noonan

[57] ABSTRACT

An instrument is disclosed for dilating the pupil of an eye. The instrument includes a handle and a switch mounted on the handle for alternating between first and second states. A retractable dilator mechanism is attached to the switch and is extendible from the handle. The dilator mechanism selectively alternates between a retracted condition when the switch is in a first state and an expanded condition when the switch is in its second state. The dilator mechanism includes hooks, a nylon ribbon or an inflatable spiral tube for engaging a plurality of points along an inside edge of the pupil and urging the pupil into a dilated condition when the dilator mechanism is expanded.

12 Claims, 4 Drawing Sheets

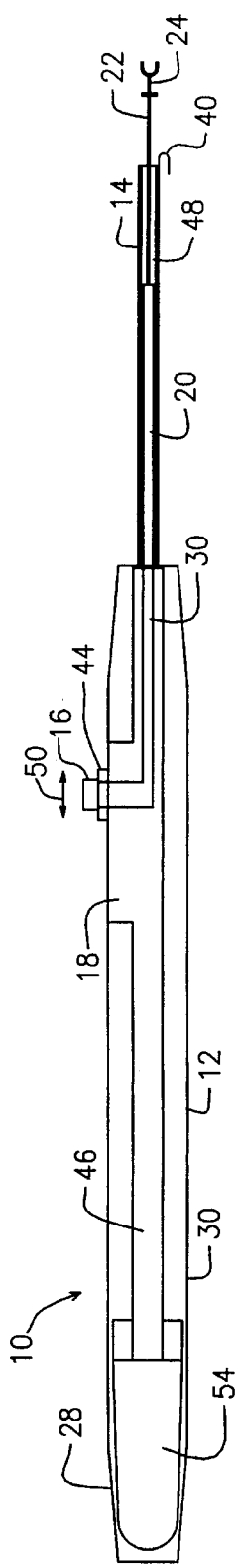
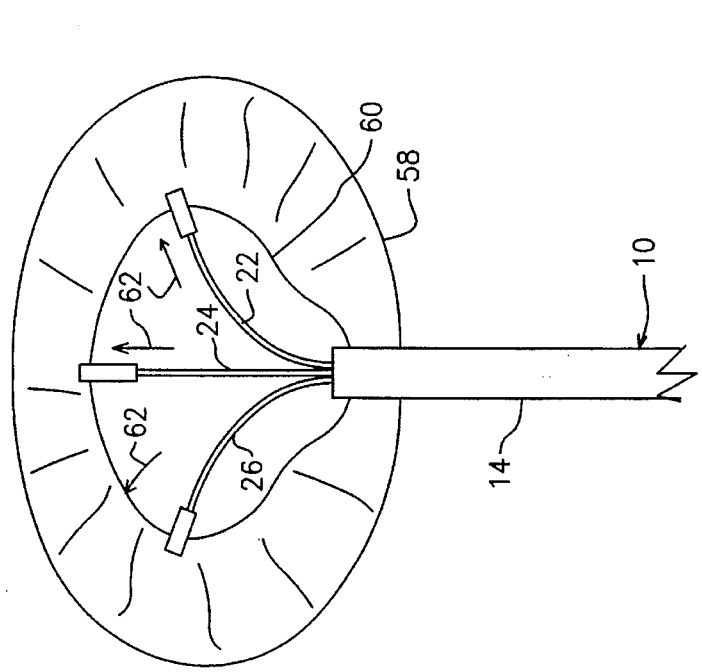
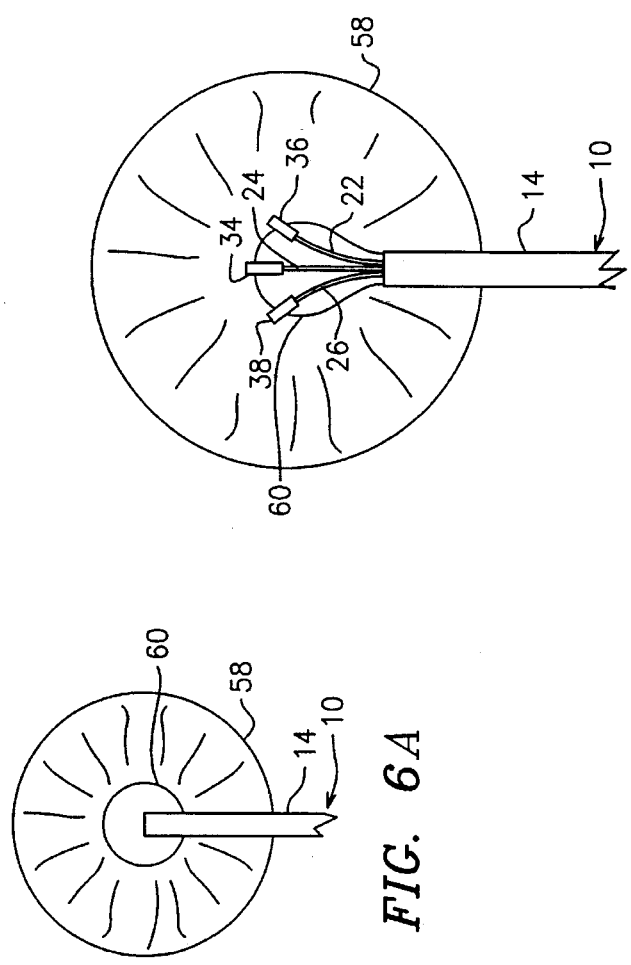
FIG. 5
FIG. 6A
FIG. 6B
FIG. 7

PUPIL DILATOR

FIELD OF THE INVENTION

This invention relates to a pupil dilator and, more particularly, to an instrument for dilating the pupil of the human eye so that the lens can be accessed for cataract surgery.

BACKGROUND OF THE INVENTION

In cataract surgery the pupil of the eye must first be dilated so that the surgeon has access to the lens. In many cases, conventional pupil dilating drugs are ineffective for this purpose. For example, if the patient has been undergoing glaucoma treatments he or she may very well have been using a myotic drug. Prolonged use of such medication tends to make the pupil fibrotic and resistant to dilation. Accordingly, in such cases, the cataract surgeon must mechanically dilate the pupil prior to surgery.

Conventional techniques for mechanically dilating the pupil exhibit various disadvantages. Typically, known mechanical dilators employ an intricate construction and are often quite difficult for the surgeon to manipulate and set in place. For example, in one technique, four retractors are surgically implanted into the eye. Each retractor includes a hook that holds a corner of the pupil in such a way that a square opening is created. In addition to being time consuming, complicated and expensive, this technique requires that four incisions be made in the eyeball. Precise manipulation of the iris is also required.

In another known technique, a water absorbent ring is inserted into the pupil. As the ring absorbs liquid and expands, it conforms to the shape of the pupil and causes it to dilate. This ring is difficult to introduce into and remove from the pupil. Additionally, it needs to be precisely manipulated in the eye by the surgeon.

SUMMARY OF INVENTION

It is therefore an object of this invention to provide an improved instrument for dilating the pupil of the human eye so that the lens is accessible for cataract surgery;

It is a further object of this invention to provide a mechanical pupil dilator that is quickly and conveniently introduced into the pupil of the eye and operated by the surgeon to open the pupil a desired amount;

It is a further object of this invention to provide a mechanical pupil dilator that employs a relatively simple, yet effective construction;

It is a further object of this invention to provide a mechanical pupil dilator that effectively opens the pupil without requiring additional incisions in the eye.

This invention features an instrument for dilating the pupil of an eye, including a handle and switch means mounted on the handle for alternating between first and second states. A retractable dilator mechanism is attached to the switch means and is extendible from the handle. The dilator mechanism selectively alternates between a retracted condition when the switch means are in a first state and an expanded condition when the switch means are in the second state. Engagement means are carried by the dilator mechanism for engaging a plurality of points along an inside edge of the pupil and urging the pupil into a dilating condition when the dilator mechanism is expanded.

In a preferred embodiment the switch means include a manually engageable switch element that is slidably mounted on the handle. The handle may include an internal channel that slidably receives at least a portion of the dilator mechanism and a longitudinal groove connected to the internal channel for receiving the switch element.

The dilator mechanism may include a plurality of elongate arms. The engagement means may include hook elements that are respectively secured to the distal end of each arm. The arms may be longitudinally slidably receivable in a tubular sheath that is secured to and extends from the handle. The arms retract into the sheath when the switch means are moved into the first state and expand out of the sheath when switch means are moved into the second state. A plurality of such arms may be resiliently curved such that the arms expand radially when they are extended out of the sheath and contract radially when the arms are retracted into the sheath. The dilator mechanism may include an elongate shaft that interconnects the switch means and the elongate arms. The shaft is slidably receivable in the channel and the tubular sheath. A tensioning hook may be carried by the sheath for engaging and tensioning the pupil when the dilator mechanism is expanded.

In an alternative embodiment, the dilator mechanism may comprise an elongate ribbon that is attached to the switch element and slidably received in a guide that is attached to the handle. The ribbon may have a distal end that is attached to a distal portion of the handle and a loop section that is formed beyond the distal end of the handle. The engagement means are preferably defined by the loop portion of the ribbon.

In another alternative embodiment, the dilator mechanism may include a piston that is mounted in the handle and responsive to movement of the switch member. The dilator mechanism may also include a pneumatic cylinder for operably receiving the piston, a selectively inflatable and deflatable coil element and a pneumatic conduit interconnected between the cylinder and the coil element. In the first switch state, the piston is retracted in the cylinder and the coil element is collapsed. In the second switch state, the piston compresses air in the cylinder and the coil element is expanded. In this embodiment, the engagement means are preferably defined by an outer surface of the coil element.

DETAILED DESCRIPTION OF PREFERRED EMBODIMENTS

Other objects, features and advantages will occur from the following description of preferred embodiments and the accompanying drawings, in which:

FIG. 5 is an elevational cross sectional view of the instrument of FIGS. 1 and 2;

FIG. 6A is an elevational plan view of the forward end of the dilator instrument inserted in the undilated pupil of a human eye and with the dilator mechanism fully retracted;

FIG. 6B is a view, similar to FIG. 6A, of the dilator mechanism in a partially expanded condition with the hook elements engaging the inside edge of the pupil of an eye;

FIG. 7 is a view, similar to FIG. 6A, of the dilator instrument engaging the pupil of an eye and with the dilator mechanism in a fully expanded condition, which dilates the pupil.

Figure 1:
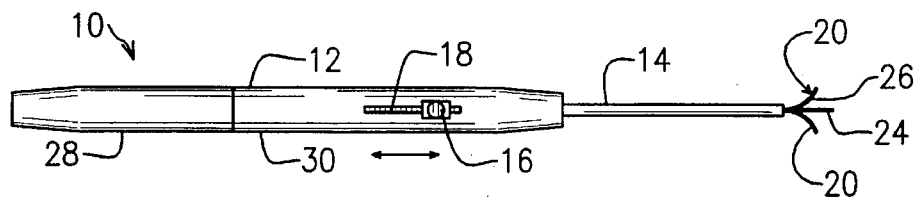
FIG. 1 is a plan view of a preferred pupil dilating instrument according to this invention.
Figure 2:
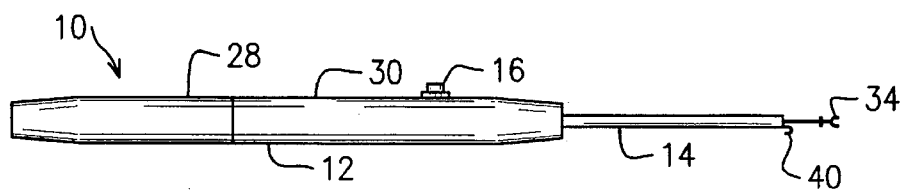
FIG. 2 is an elevational side view of the instrument of FIG. 1.

There is shown in FIGS. 1 and 2 a mechanical pupil dilating instrument 10. The instrument includes an elongate handle 12 and an elongate tubular sheath 14 that is attached to and extends from the forward end of handle 12. A thumb activated switch 16 is movably mounted to handle 12. In particular, switch 16 engages handle 12 through a longitudinal groove 18 formed in the handle. Switch 16 is slidable between a first state or position at the rearward end of groove 18 and a second state or position at the forward end of the groove. As is described more fully below, the switch is attached 20 inside of handle 12 to a retractable dilator mechanism. The dilator mechanism extends from the forward end of the handle through sheath 14 and emerges from the distal end of the sheath. Dilator mechanism 20 includes three resilient wires 22, 24 and 26, which engage the pupil to be dilated. The precise construction and operation of these elements is explained more fully below.

Handle 12 comprises a pair of molded plastic portions 28 and 30. The switch and sheath may similarly comprise durable yet light weight plastics or other materials that are commonly used for surgical instruments. The handle may comprise configurations other than that shown and may exhibit a one piece or other multiple piece construction.

Figure 3:
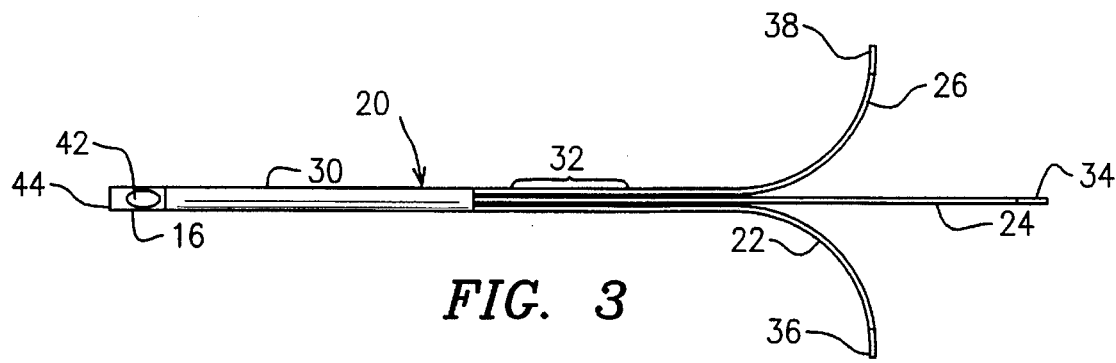
FIG. 3 is a plan view of the retractable dilator mechanism employed in the instrument of FIGS. 1 and 2.
Figure 4:
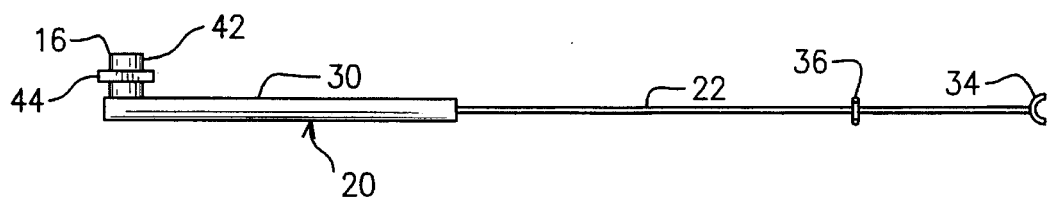
FIG. 4 is an elevational side view of the mechanism of FIG. 3.

Retractable dilator mechanism 20 and attached thumb switch 16 are illustrated in greater detail in FIGS. 3 and 4. The dilator mechanism includes an elongate shaft 30 that is preferably composed of a plastic or other synthetic material. Resilient wires 22, 24 and 26 are secured to a forward end of shaft 30. The ends of the wires proximate shaft 30 are juxtaposed and aligned. Central wire 24 extends in an linearly for its entire length. Adjacent wires 22 and 26 diverge in a generally Y-shaped configuration from wire 24 prior to their distal ends. Wires 22 and 26 are provided with a spring bias that causes them to diverge from the axis defined by wire 24. The degree of divergence is determined by the length of wires 22, 24 and 26 exposed from sheath 14, FIGS. 1 and 2. The wire segments located within the sheath are held together in a non-divergent condition as shown, for example, by segments 32 in FIG. 3. Any portion of the mechanism 20 that is exposed from sheath 14 is biased into the divergent condition. Therefore, the radial size defined by mechanism 20 expands as more of the dilator mechanism is exposed from the sheath.

The distal end of each wire carries a respective engagement means in the form of a U-shaped hook. Wire 24 carries a hook 34. Similarly, wire 22 carries a hook 36 and wire 26 carries a hook 38. The hooks are quite small, as illustrated by hook 34 in FIG. 2, so that they are able to engage an inner edge of the pupil of a patient's eye. A tensioning hook 40 is carried by sheath 14. As described below, hook 40 engages the inside edge of the patient's pupil as the dilator instrument is operated. This tensions and helps to dilate the pupil.

Referring to FIGS. 3 and 4, each of the wires 22, 24, and 26 is secured to shaft 30 such as by embedding the wires into the shaft as it is molded, appropriate adhesives or in other manners that will be known to those skilled in the art. Switch 16 is secured unitarily or otherwise to the opposite end of shaft 30. The switch includes a thumb engaging portion 42 and a slide portion 44. The thumb engaging portion should have a size and shape such that it is comfortably engageable by the surgeon during a cataract operation.

As shown in FIG. 5, handle 12 has a longitudinal internal channel 46 that is communicably interconnected with longitudinal groove 18. Tubular sheath 14 has a central channel 48 that is communicably aligned with channel 46. Elongate shaft 30 of dilator mechanism 20 extends between channels 46 and 48. Resilient wires 22, 24 and 26 (the latter of which is obscured) extend from the distal end of shaft 20 through channel 48 emerge from the distal end of sheath 14. Thumb switch 16 extends upwardly from shaft 30 through groove 18. Slide portion 44 of switch 16 engages the handle adjacent to groove 18. As a result, the surgeon operates instrument 10 by engaging switch 16 and moving the switch forwardly or rearwardly, as required, in the manner indicated by double headed arrow 50. As switch 16 is moved forwardly, shaft 30 is pushed toward the distal end of sheath 14. Wires 22, 24 and 26 gradually emerge from sheath 14 and expand in a divergent manner. Subsequently, the wires may be retracted within the sheath by pushing switch 16 rearwardly into its opposite state. The resilient wires 22 and 26 collapse as they are gradually drawn into sheath 14.

The opposite end of handle 12 includes a portion 28 that is molded and has an internal cavity 54. Parts 28 and 30 are secured together either permanently or provisionally by adhesives, sonic welding, threads or other known attachment means.

Instrument 10 is used in cataract surgery, as illustrated in FIGS. 6A, 6B and 7 to expand pupil 60 of eye 58. First, the patient is anesthetized and prepared for surgery. The surgeon grasps the handle 12 of instrument 10 and pushes switch 16 rearwardly, into its first state, as previously described, so that the dilator mechanism is fully retracted. In that condition, the wires are drawn fully into sheath 14, in the manner shown in FIG. 6A. The surgeon then manipulates instrument 10 and interengages hook 40 (which is obscured in FIG. 6B) with the inside edge of pupil 60. Instrument 10 is pulled in the direction of arrow 61 to tension pupil 60. Engagement hooks 34, 36 and 38 are partly expanded by pushing switch 16 in a forward direction such that the hooks likewise engage and grip the inner edge of pupil 60 (FIG. 6B). The small, radially compact size of the wires makes insertion quick and convenient. After secure engagement is made, the surgeon slides switch 16 fully forwardly into its second state. This pushes wires 22, 24 and 26 outwardly from the distal end of sheath 14 in the manner shown in FIG. 7. At the same time, hook 40 maintains its engagement with the edge of pupil 60 and tension is maintained in the direction of arrow 61. The resiliently biased wires 22, 24 and 26 diverge as indicated by arrows 62. As a result, pupil 60 is opened or dilated. The surgeon is then able to perform necessary repair or replacement of the lens. After the pupil 60 is dilated in this manner, instrument 10 is quickly and conveniently removed from the vicinity of the eye by retracting wires 22, 24 and 26, as described above, such that the hooks 34, 36 and 38 disengage the edges of pupil 60. During the dilation process, the fibrosis in the eye is broken. Therefore, the pupil remains dilated even after the U-shaped hooks and the tensioning hook are disengaged from the pupil and the wires are retracted. As a result, unlike many conventional pupil dilators, the instrument does not have to remain engaged with the eye during cataract or other eye surgery.

Figure 8A:
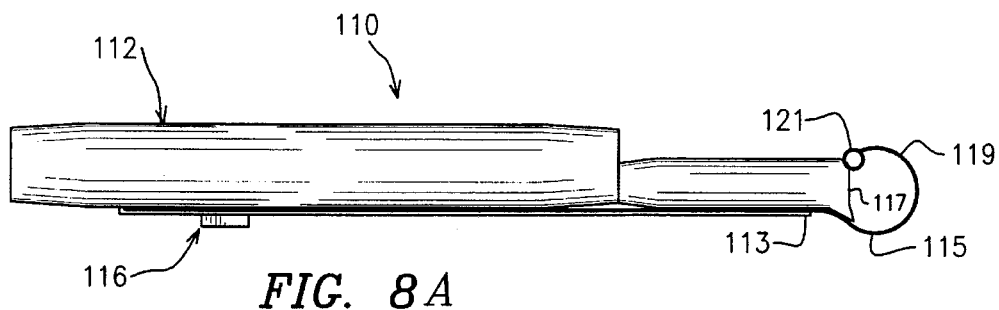
FIG. 8A is a plan view of an alternative pupil dilating instrument according to this invention, wherein a thin ribbon is employed as the dilator mechanism.
Figure 8B:
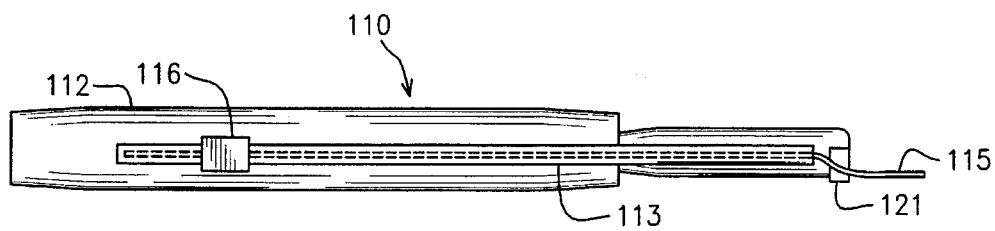
FIG. 8B is an elevational side view of the instrument of FIG. 8A.

FIGS. 8A and 8B illustrate an alternative pupil dilating instrument 110. The instrument comprises a handle 112 that is formed of molded plastic or other rugged, yet lightweight material. An elongate metal or plastic guide 113 is mounted longitudinally along the side of handle 112. An elongate nylon ribbon 115 is received in a space between guide 113 and handle 112. Ribbon 115 extends beyond a forward end 117 of handle 112 and forms a loop 119. The distal end of nylon ribbon 115 is connected to handle 112 by a pivot 121.

Figure 9:
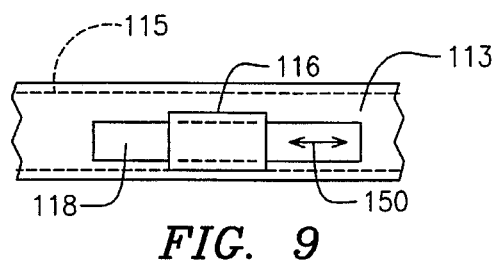
FIG. 9 is an elevational view of the switch and ribbon guide used in the instrument of FIGS. 8A and 8B.

A switch 116 is slidably mounted to handle 112. As best illustrated in FIG. 9, the switch is attached to nylon ribbon 115 through a longitudinal groove 118 in ribbon guide 113. As a result, thumb switch 116 is able to slide back and forth in the direction of double headed arrow 150. Other alternative means may be employed for slidably mounting switch 116 to housing 112 and for attaching the switch to the nylon ribbon.

When switch 116 is moved to a rearward position in groove 118, ribbon 115 is retracted in ribbon guide 113 and loop 119 maintains the relatively small, contracted circular shape shown in FIGS. 8A and 8B. When switch 116 is pushed forwardly, ribbon 115 is driven through guide 113 and loop 119 is expanded and enlarged.

Figure 10:
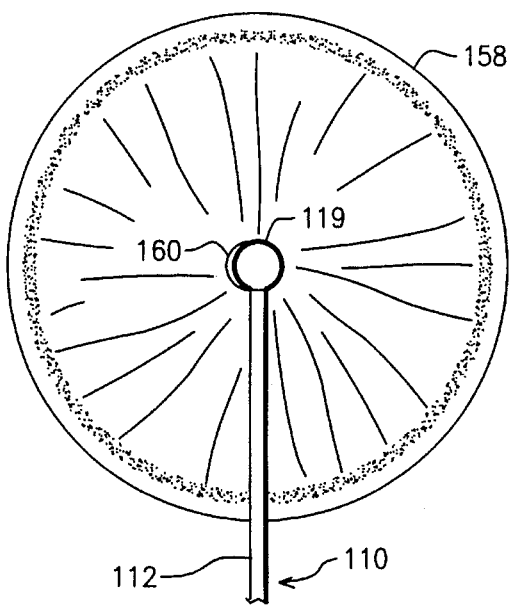
FIG. 10 is a plan view of the leading end of the instrument of FIGS. 8A and 8B inserted in a pupil of the human eye and maintaining a collapsed or retracted condition prior to the dilation of the pupil.
Figure 11:
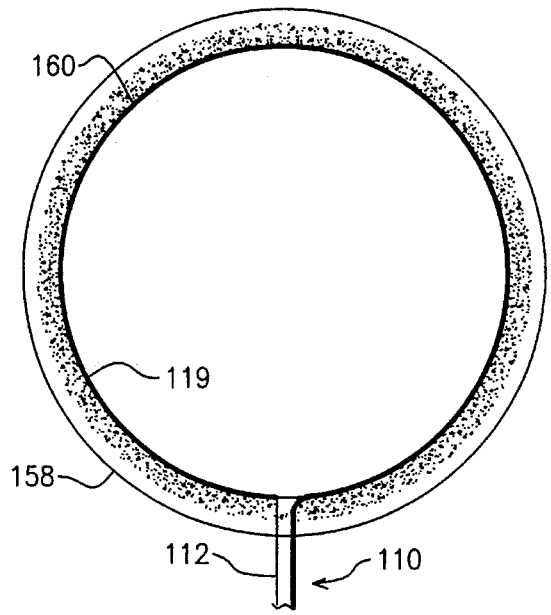
FIG. 11 is a view similar to FIG. 10 of the dilating instrument in an expanded condition, which dilates the pupil.

FIG. 10 depicts instrument 110 with loop 119 in a retracted condition. In this condition, instrument 110 is conveniently manipulated by the surgeon such that loop 119 is placed within pupil 160 of eye 158. An outer circumferential surface of loop 119 forms an engagement means which engages the inner edge of pupil 160. To dilate the pupil, switch 116 is pushed forwardly relative to handle 112 in the manner described in FIGS. 8A, 8B and 9. This causes loop 119 to expand into the condition shown in FIG. 11. As a result, pupil 160 is dilated in the manner shown. Switch 116 is then pushed rearwardly to retract loop 119. The dilator is removed from the pupil and cataract surgery is performed.

Figure 12:
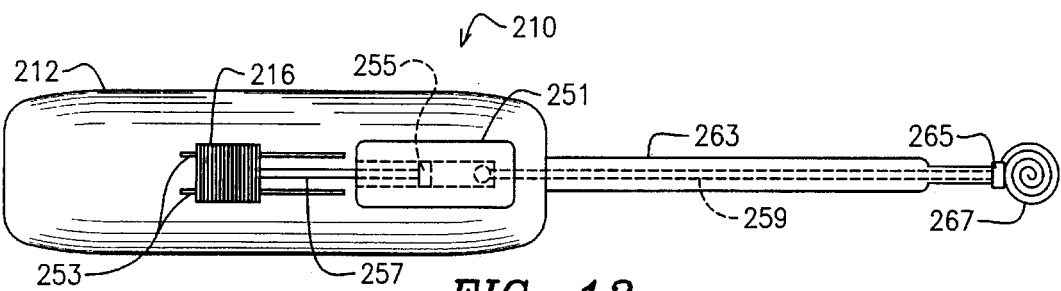
FIG. 12 is a plan view of another alternative pupil dilating instrument according to this invention, which instrument employs a pneumatically operated dilator mechanism.
Figure 13:
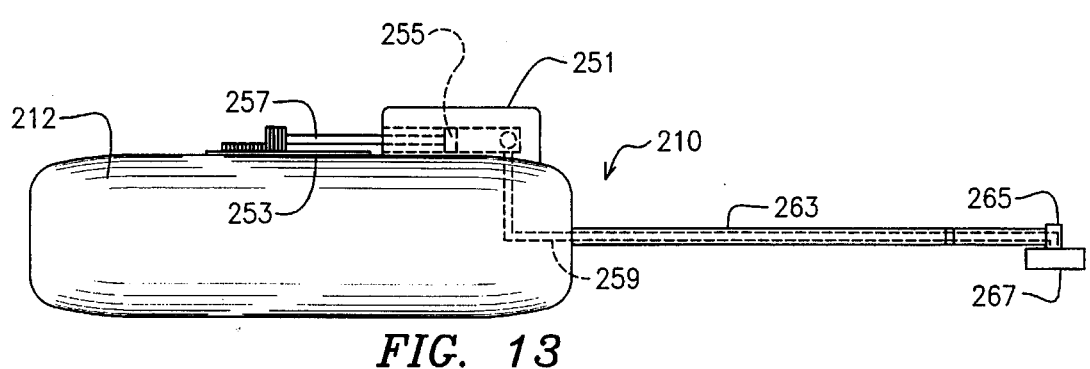
FIG. 13 is an elevational, side view of the instrument of FIG. 12.

A pneumatically powered mechanical dilator 210 is illustrated in FIGS. 12 and 13. Instrument 210 includes a handle 212 and a pneumatic cylinder 251 mounted to an upper surface of handle 212. A thumb switch 216 is slidably mounted on a track 253 formed on handle 212 adjacent to cylinder 251. A pneumatic piston 255, shown in phantom, is operably mounted within cylinder 251. An actuating rod 257 operably interconnects switch 216 and pneumatic piston 255.

Figure 14:
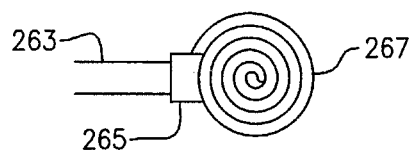
FIG. 14 is a plan view of the coil element that is utilized as the dilator mechanism of FIGS. 12 and 13, which element is in a uninflated, retracted condition.

A pneumatic conduit 259, shown in phantom, extends from cylinder 251, through the forward end of handle 212 and through an elongate extension piece 263. A fitting 265 at the distal end of extension 263 interconnects the extension to an inflatable spiral tube 267. In particular, tube 267 is communicably attached to conduit 259. The spiral tube, shown alone in FIG. 14, may comprise various sterile plastic materials that are suitable for use in opthamalogical and surgical applications.

Switch 216 is selectively slid back and forth along tracks 253 between a rearward, first state and a forward, second state. In the first state, rod 257 retracts piston 245 in cylinder 251. As a result, air is not compressed in the cylinder or the pneumatic conduit. This causes spiral tube 267 to remain deflated and in the contracted condition shown in FIGS. 12, 13 and 14. Conversely, if switch 216 is slid forwardly into its second state, piston 255 is driven forwardly in cylinder 251 to compress air in the cylinder. This causes air pressure to be transmitted through conduit 259 into spiral tube 267. The spiral tube inflates or expands to dilate the patient's pupil.

Figure 15:
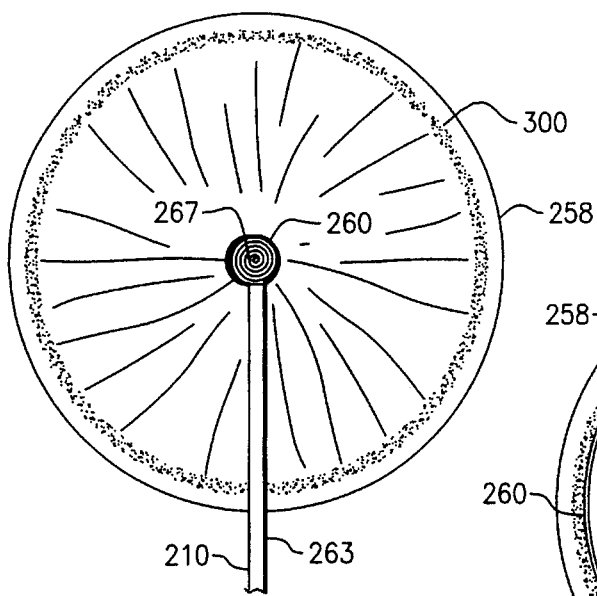
FIG. 15 is a plan view of the instrument of FIGS. 12–14 with the deflated coil element introduced into the pupil of an undilated eye.
Figure 16:
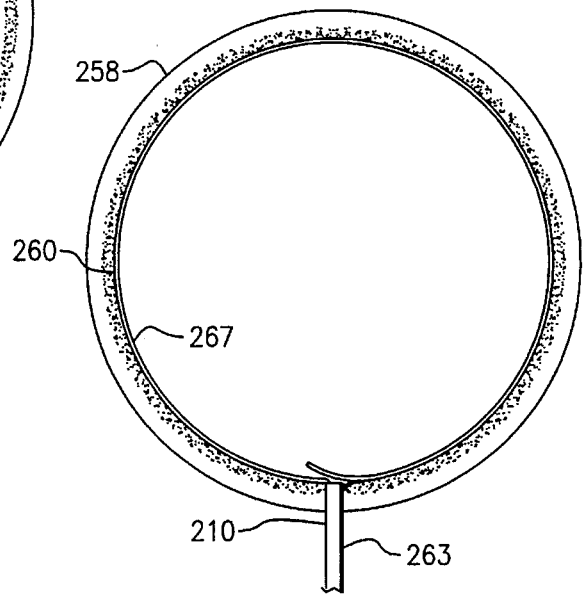
FIG. 16 is a view similar to that shown in FIG. 15 but with the coil element in s pneumatically expanded condition, which causes the pupil to dilate.

Instrument 210 is specifically utilized in the manner shown in FIGS. 15 and 16 in order to dilate pupil 260 of eye 258. Initially, as shown in FIG. 15, instrument 210 is positioned inside eye 258 such that spiral tube 267 is introduced into pupil 260. The contracted condition of tube 267 permits the dilator instrument to be readily manipulated by the surgeon and positioned within the pupil. Subsequently, the surgeon actuates the dilator by sliding switch 216 forwardly. This causes tube 267 to expand, as previously described, into the condition shown in FIGS. 16. The outer surface of the spiral tube engages the inner edge of pupil 260. As tube 267 is inflated, it radially expands in the manner shown, to dilate the pupil. As with each of the instruments described herein, this entire dilating operation is accomplished almost immediately and does not require the manipulation and/or surgical insertions required by dilators of the prior art.

Accordingly, the present invention accomplishes improved rapid dilation of the pupil so that cataract surgery and other eye procedures can be performed rapidly and effectively. In each of the embodiments described herein, time is saved and surgery is facilitated because the surgeon does not have to perform tedious manipulations and attachments of an instrument to the pupil. Additionally, the incisions do not have to be made in the eye to attach the instrument. As in the initially described embodiment, the instruments of the other embodiments can be removed as soon as dilation is performed because at that point, the fibrosis in the eye is broken and the pupil should remain dilated for the duration of the surgery.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. An instrument for dilating the pupil of an eye comprising:

a handle;

switch means mounted on said handle for alternating between first and second states;

a retractable dilator mechanism including a plurality of elongate arms attached to said switch means and being extendible from said handle, said dilator mechanism selectively alternating between a retracted condition when said switch means are in said first state and an expanded condition when said switch means are in said second state; and engagement means carried by said dilator mechanism, and including hook elements that are respectively secured to a distal end of each said arm, for engaging a plurality of points along an inside edge of the pupil and urging said pupil into a dilated condition when said dilator mechanism is expanded.

2. The instrument of claim 1 in which said switch means include a manually engageable switch element that is slidably mounted on said handle.

3. The instrument of claim 2 in which said handle includes an internal channel that slidably receives at least a portion of said dilator mechanism and a longitudinal groove connected to said internal channel for receiving, said switch element.

4. An instrument for dilating the pupil of an eye comprising:

a handle;

switch means mounted on said handle for alternating between first and second states;

a retractable dilator mechanism including a plurality of elongate arms attached to said switch means and being extendible from said handle, said dilator mechanism selectively alternating between a retracted condition when said switch means are in said first state and an expanded condition when said switch means are in said second state, said arms being longitudinally slidably receivable in a tubular sheath that is secured to and extends from said handle; said arms retracting into said sheath when said switch means are moved into said first state and expanding out of said sheath when said switch means are moved into said second state;

engagement means carried by said dilator mechanism for engaging a plurality of points along an inside edge of the pupil and urging said pupil into a dilated condition when said dilator mechanism is expanded; and a tensioning hook carried by said sheath for engaging and tensioning said inside edge of said pupil as said dilator mechanism is expanded.

5. The instrument of claim 4 in which said dilator mechanism includes a plurality of elongate arms.

6. The instrument of claim 5 in which said engagement means include hook elements that are respectively secured to a distal end of each said arm.

7. The instrument of claim 5 in which said arms are longitudinally slidably receivable in a tubular sheath that is secured to and extends from said handle; said arms retracting into said sheath when said switch means are moved into said first state and expanding out of said sheath when said switch means are moved into said second state.

8. The instrument of claim 7 in which a plurality of said arms are resiliently curved such that said arms expand radially when said arms are extended out of said sheath and collapse radially when said arms are retracted into said sheath.

9. The instrument of claim 8 in which said handle includes an internal channel that is communicably aligned with said sheath and receives at least a portion of said dilator mechanism.

10. The instrument of claim 9 in which said dilator mechanism includes an elongate shaft that interconnects said switch means and said elongate arms and is slidably received in said channel and said tubular sheath.

11. The instrument of claim 7 further including, a tensioning, hook carried by said sheath for engaging and tensioning said inside edge of said pupil as said dilator mechanism is expanded.

12. A method of dilating the pupil of an eye, said method comprising:

providing a pupil dilating instrument, which includes a handle, switch means mounted on said handle for alternating between first and second states, a retractable dilator mechanism attached to said switch means and being extendible from said handle, said dilator mechanism being selectively alternatable between a retracted condition when said switch means are in a first state and an expanded condition when said switch means are in said second state, and means carried by said dilator mechanism for selectively engaging an inside edge of the pupil;

positioning said instrument proximate the pupil with said switch means in said first state and interengaging said means for engaging with a plurality of points along the inside edge of the pupil; and alternating said switch from said first state to said second state to expand said dilator mechanism and urge the pupil into a dilated condition.

* * * * *